(12) United States Patent
Ruan et al.

(10) Patent No.: US 10,718,015 B2
(45) Date of Patent: Jul. 21, 2020

(54) SEQUENCING LIBRARY, PREPARATION METHOD AND USE THEREOF

(71) Applicant: Beijing Institute of Genomics, Chinese Academy of Sciences, Beijing (CN)

(72) Inventors: Jue Ruan, Beijing (CN); Kaile Wang, Beijing (CN); Chung-I Wu, Beijing (CN); Xuemei Lu, Beijing (CN)

(73) Assignee: Beijing Institute of Genomica, Chinese Academy of Sciences, Beijing (CN)

( * ) Notice: Subject to any disclaimer, the term of this patent is extended or adjusted under 35 U.S.C. 154(b) by 592 days.

(21) Appl. No.: 15/101,605

(22) PCT Filed: Dec. 5, 2014

(86) PCT No.: PCT/CN2014/093161
§ 371 (c)(1),
(2) Date: Jun. 3, 2016

(87) PCT Pub. No.: WO2015/081890
PCT Pub. Date: Jun. 11, 2015

(65) Prior Publication Data
US 2016/0362735 A1    Dec. 15, 2016

(30) Foreign Application Priority Data
Dec. 6, 2013 (CN) .......................... 2013 1 0651462

(51) Int. Cl.
*C12Q 1/6869* (2018.01)
*C12N 15/10* (2006.01)
(Continued)

(52) U.S. Cl.
CPC .......... *C12Q 1/6869* (2013.01); *C12N 15/10* (2013.01); *C12Q 1/6844* (2013.01); *C12N 2310/51* (2013.01); *C12Q 2537/155* (2013.01)

(58) Field of Classification Search
CPC .. C12N 15/10; C12N 2310/51; C12Q 1/6844; C12Q 1/6869; C12Q 2537/155
See application file for complete search history.

(56) References Cited

U.S. PATENT DOCUMENTS

2009/0176280 A1    7/2009    Hutchison, III et al.
2011/0003701 A1    1/2011    Ferreri et al.

FOREIGN PATENT DOCUMENTS

CN       101213311        7/2008
WO       2009/106308      9/2009

OTHER PUBLICATIONS

Margulies et al., Nature, 437:375-380 (Year: 2005).*
(Continued)

*Primary Examiner* — Jeremy C Flinders
(74) *Attorney, Agent, or Firm* — Honigman LLP; Thomas A. Wooten, Esq.; Honathan P. O'Brien

(57) ABSTRACT

The present invention provides a sequencing library, and the sequencing library has an inserted fragment which is an equidirectional alternating concatemer of a sequence to be tested and a tag sequence. The present invention further provides a method for preparing the sequencing library. The present invention also provides a sequencing method. The sequencing library and sequencing method as provided in the present invention are capable of removing DNA amplification errors and sequencing errors under any sequencing depths, so that mutations of DNA molecules could be ultra-accurately determined. The sequencing library of the
(Continued)

present invention is suitable for construction of a sequencing library of trace short DNA fragments and even of single-strand DNAs.

17 Claims, 1 Drawing Sheet

Specification includes a Sequence Listing.

(51) Int. Cl.
  *C12Q 1/6844* (2018.01)
  *C12Q 1/48* (2006.01)

(56) References Cited

OTHER PUBLICATIONS

Lou et al. (Proc. Natl. Acad. Sci., 110(49):19872-19877) (Year: 2013).*
Wong et al. (Curr Protoc Mol Biol., Chapter 7:Unit 7.11) (Year: 2013).*
Rohland et al. (Genome Research, 2012, 22:939-946) (Year: 2012).*
Invitrogen (GeneCatcher™ gDNA Blood Kit product information sheet) (Year: 2006).*
Schmitt et al. (Proc. Natl. Acad. Sci., 2012, 109(36):14508-14513) (Year: 2012).*
Of Wapenaar et al. (Exon Trapping (2001) In: Starkey M.P., Elaswarapu R. (eds) Genomics Protocols. Methods in Molecular Biology™, vol 175. Humana Press) (Year: 2001).*
Isaac Kinde et al., "Detection and quantification of rare mutations with massively parallel sequencing", PNAS, 108(23):9530-9535, 2011.
Roger S. Lasken, "Genomic DNA amplification by the multiple displacement amplification (MDA) method", Biochemical Society Transactions, 37(Pt. 2):450-453, 2009.

* cited by examiner

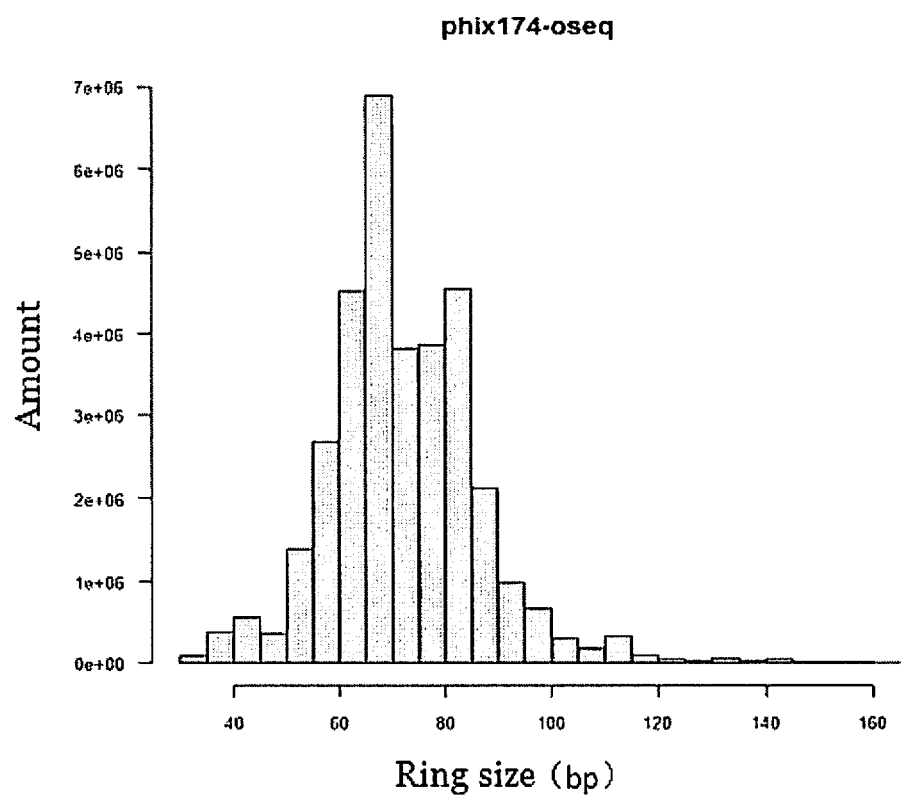

SEQUENCING LIBRARY, PREPARATION METHOD AND USE THEREOF

CROSS-REFERENCE TO RELATED APPLICATIONS

This application claims priority under 35 U.S.C. § 371 to Patent Cooperation Treaty application PCT/CN2014/093161, filed Dec. 5, 2014, which claims the benefit of Chinese Patent Application No. 201310651462.5, filed Dec. 6, 2013, the entire contents of which are incorporated herein by reference.

SEQUENCE LISTING

This application incorporates by reference in its entirety the Sequence Listing entitled "2016-06-22_IEC140067PUS_235427-396007.txt" (2.97 kilobytes), which was created on Jun. 22, 2016, and filed electronically herewith.

TECHNICAL FIELD

The present invention relates to a sequencing library, and a preparation method and use thereof.

BACKGROUND ART

The development of the second-generation sequencing technology promotes the revolutionary development of biology and biomedical research. However, about 1% bases are not correctly sequenced due to natural characteristics of high-throughput sequencing. Although 1% error rate is tolerable in some applications, these 1% base errors may cover up lots of real information and hinder researches in many situations, for example, determining whether a tissue or organ of a normal individual has potential carcinogenic mutation sites, determining heterogenicity of DNA composition and latent small clone colonies in cancer cell colonies, tracing origin and division pattern of a cell by using a DNA mutation as label in the cell, accurately obtaining genotype of a highly-hybridized cancer colony, calculating rate of mutation generation during division of cancer cells or somatic cells, finding pathogenic mutations in some small colonies (e.g., cancer stem cells) during biomedical therapy. Hence, it is a very vital problem on how to accurately determining DNA sequence by using currently available second-generation sequencing technologies.

So far, some attempts have been carried out to reduce errors of the second-generation sequencing from biological and chemical aspects. For example, non-amplification library building method can effectively avoid errors generated during polymerase chain reaction amplification in preparation of library; and chain-specific errors can be effectively screened by adding labels to sample DNA and reference DNA. Further, some methods try to reduce error rate of the second-generation sequencing from perspective of data analysis. In addition, some other methods try to rectify errors generated during polymerase chain reaction amplification by using breakpoint information of random DNA breaks or adding labels to DNA template prior to polymerase chain reaction amplification, wherein it can be determined by adding labels which DNA molecules are derived from the same template, and thus rectification is achieved.

These methods improve the accurateness of the second-generation sequencing to a certain extent, but still have drawbacks respectively. For example, Kinde, et al., (Kinde I, Wu J, Papadopoulos N, Kinzler K W, Vogelstein B (2011) Detection and quantification of rare mutations with massively parallel sequencing. Proc Natl Acad Sci USA 108: 9530-9535), report that the addition of labels is carried out by adding labels at terminals of specific primers and then adding labels in DNA molecules via polymerase chain reaction, thus when an error occurred in polymerase chain reaction during addition of labels, this error can hardly be removed in subsequent steps, and thus determination of extremely infrequent sites by this method is limited. One serious limitation for the method of adding exogenous labels to DNA is that this method can be merely applied to small genomes or a small number of target genes, and cannot be used for comprehensive determination of a whole genome. The reason for this is that mutual rectification of DNA positive and negative chains can be carried out in the labeling method only when identical and complementary labels are determined, which requires a great sequencing depth that can hardly be achieved for a large genome.

In the meantime, since peripheral blood can be readily collected without invasive effects to body and its mutation information reflects real mutation of individual to a certain extent, determination of mutation information of free DNAs in peripheral blood is widely used in antenatal diagnosis and cancer surveillance. However, when free DNAs in peripheral blood are degraded into 140-170 base-pairs and only thousands copies exist in 1 milliliter of blood. Therefore, a problem to be solved is that how to build DNA libraries effectively using such a little amount of DNA, how to determine an extremely infrequent mutation in free DNAs of peripheral blood by using a limited sequencing coverage.

Most of fossil DNAs are contaminated by microorganism and such DNAs are of a very small amount and seriously degraded. Therefore, a problem in studying ancient human DNAs is how to effectively build second-generation high-throughput sequencing libraries and effectively enrich ancient human DNAs by using a very small amount of seriously degraded fossil DNAs.

In sum, it is necessary to build DNA sequencing libraries for rapid, effective and accurate sequencing.

CONTENTS OF THE INVENTION

In order to solve the problem that the DNA sequencing precision in the prior art cannot meet actual needs, the present invention provides a sequencing library and methods for preparing and using the same.

The first aspect of the present invention relates to a sequencing library, characterized in that the sequencing library has an inserted fragment comprising an equidirectional alternating concatemer of a sequence to be tested and a tag sequence.

In the present invention, the tag sequence can be linked to 5'-terminal or 3'-terminal of the sequence to be tested.

In one embodiment of the present invention, the tag sequence is linked to 5'-terminal of the sequence to be tested.

The sequencing library according to any one of items of the first aspect of the present invention, is preferably characterized in that, the sum of the length of each sequence to be tested and length of the tag sequence is less than half of the sequencing length of a sequencer.

The sequencing library according to any one of items of the first aspect of the present invention, is preferably characterized in that, the equidirectional alternating concatemer has a length greater than the sequencing length of a sequencer.

In one embodiment of the present invention, the equidirectional alternating concatemer comprises at least two repetitive units, and each repetitive unit comprises one sequence to be tested and one tag sequence.

The sequencing library according to any one of items of the first aspect of the present invention, is preferably characterized in that, the tag sequence comprises 4-20 (e.g., 6-13) consecutive determined bases and 0-18 (e.g., 0-13) consecutive random bases.

The sequencing library according to any one of items of the first aspect of the present invention, is preferably characterized in that, the determined bases and the random bases are arranged in a mode of sequential arrangement (the determined bases are arranged in front of or behind the random bases) or mosaic arrangement.

The sequencing library according to any one of items of the first aspect of the present invention, wherein the sequencing library is preferably used for a second-generation sequencing or a third-generation sequencing.

The second aspect of the present invention relates to a method for preparing a sequencing library, comprising the following steps:

(1) a sequence to be tested is linked to a tag sequence to obtain a double-strand or single-strand linked sequence;

(2) when the linked sequence obtained in step (1) is a double-strand sequence, the linked sequence is converted into single-strand sequences, then cyclized; when the linked sequence obtained in step (1) is a single-strand sequence, the linked sequence is directly cyclized;

(3) the cyclized linked sequence obtained in step (2) is subjected to DNA amplification based on strand displacement reaction to obtain an equidirectional alternating concatemer of a sequence to be tested and a tag sequence;

(4) the equidirectional alternating concatemer is fragmented, and sequencing adaptors are linked to both terminals of each resulted fragment to obtain a sequencing library.

In the method according to any one of items of the second aspect of the present invention, preferably, the sum of the length of the sequence to be tested and the length of the tag sequence is less than half of the sequencing length of a sequencer.

In the present invention, the tag sequence can be linked to 5'-terminal or 3'-terminal of the sequence to be tested.

In one embodiment of the present invention, the tag sequence is linked to 5'-terminal of the sequence to be tested.

In the method according to any one of items of the second aspect of the present invention, preferably, the resulted fragment in step (4) has a length greater than the sequencing length of a sequencer.

In one embodiment of the present invention, the equidirectional alternating concatemer comprises at least two repetitive units, and each repetitive unit comprises one sequence to be tested and one tag sequence.

In the method according to any one of items of the second aspect of the present invention, preferably, the tag sequence comprises 4-20 (e.g., 6-13) consecutive determined bases and 0-18 (e.g., 0-13) consecutive random bases.

In the method according to any one of items of the second aspect of the present invention, preferably, the determined bases and the random bases are arranged in a mode of sequential arrangement (the determined bases are arranged in front of or behind the random bases) or mosaic arrangement.

In the method according to any one of items of the second aspect of the present invention, preferably, the sequencing library is used for a second-generation sequencing or a third-generation sequencing.

The third aspect of the present invention relates to a sequencing method, comprising a step of using the sequencing library according to any one of items of the first aspect of the present invention.

The fourth aspect of the present invention relates to a sequencing method, comprising a process of preparing a sequencing library, wherein the process for preparing the sequencing library comprising the following steps:

(1) a sequence to be tested is linked to a tag sequence to obtain a double-strand or single-strand linked sequence;

(2) when the linked sequence obtained in step (1) is a double-strand sequence, the linked sequence is converted into single-strand sequences, then cyclized; when the linked sequence obtained in step (1) is a single-strand sequence, the linked sequence is directly cyclized;

(3) the cyclized linked sequence obtained in step (2) is subjected to DNA amplification based on strand displacement reaction to obtain an equidirectional alternating concatemer of the sequences to be tested and the tag sequences, that is, a sequencing library is prepared and obtained;

(4) the equidirectional alternating concatemer is fragmented, and sequencing adaptors are linked to both terminals of each resulted fragment to obtain a sequencing library.

In the method according to any one of items of the fourth aspect of the present invention, preferably, the sum of the length of each sequence to be tested and length of the tag sequence is less than half of the sequencing length of a sequencer.

In the present invention, the tag sequence can be linked to 5'-terminal or 3'-terminal of the sequence to be tested.

In one embodiment of the present invention, the tag sequence is linked to 5'-terminal of the sequence to be tested.

In the method according to any one of items of the fourth aspect of the present invention, preferably, the resulted fragment in step (4) has a length greater than the sequencing length of a sequencer.

In one embodiment of the present invention, the equidirectional alternating concatemer comprises at least two repetitive units, and each repetitive units comprises one sequence to be tested and one tag sequence.

In the method according to any one of items of the fourth aspect of the present invention, preferably, the tag sequence comprises 4-20 (e.g., 6-13) consecutive determined bases and 0-18 (e.g., 0-13) consecutive random bases.

In the method according to any one of items of the fourth aspect of the present invention, preferably, the determined bases and the random bases are arranged in a mode of sequential arrangement (the determined bases are arranged in front of or behind the random bases) or mosaic arrangement.

In the method according to any one of items of the fourth aspect of the present invention, preferably, the sequencing method is a second-generation sequencing method or a third-generation sequencing method.

The present invention further relates to a use of the sequencing library according to any one of items of the first aspect of the present invention in sequencing.

In the use according to any one of items of the present invention, preferably, the sequencing is a second-generation sequencing or a third-generation sequencing.

In the use according to any one of items of the present invention, preferably, the sequencing comprises, but is not limited to, genomic DNA sequencing, target fragment trapping sequencing (e.g., exon trapping sequencing), single-strand DNA fragment sequencing, fossil DNA sequencing, or sequencing free DNA in body fluid (e.g., blood, urine, saliva).

In the present invention, the term "the sequencing length of a sequencer" refers to: for paired-end sequencing, the sequencing length of a sequencer equals to sum of sequencing length at both ends; for single-read sequencing, the sequencing length of a sequencer equals to single-ended sequencing length.

In one embodiment of the present invention, the tag sequence comprises random bases. In one embodiment of the present invention, the number of the random bases can be, for example, 1-13, for example, 1, 2, 3, 4, 5, 6, 7, 8, 9, 10, 11, 12, 13.

In one embodiment of the present invention, the number of the determined bases in the tag sequences can be 6-13, for example, 6, 7, 8, 9, 10, 11, 12, 13.

In the present invention, the tag sequence can be designed as 2 sequences or 1 sequence; when two tag sequences are designed, these two sequences can be annealed to form a duplex. In one embodiment of the present invention, two tag sequences are designed.

In one embodiment of the present invention, the tag sequences are shown in SEQ ID NO: 1 and/or SEQ ID NO: 2.

In one embodiment of the present invention, the tag sequences are shown in SEQ ID NO: 14 and/or SEQ ID NO: 15.

In the present invention, a double-strand sequence to be tested can be linked to a double-strand tag sequence, or a single-strand sequence to be tested can be linked to a single-strand tag sequence, so as to obtain a double-strand linked sequence or a single-strand linked sequence. If a double-strand linked sequence is obtained, it should be converted into single-strand sequences and then cyclized; if a single-strand linked sequence is obtained, it can be directly cyclized.

In one embodiment of the present invention, when the tag sequence is designed as double strand, two sequences can be annealed to obtain the double-strand tag sequence, in which one is phosphorylated at its 5'-terminal so as to link to a sequence to be tested, while the other one is not phosphorylated at its 5'-terminal, so that the finally constructed sequencing library comprises merely the phosphorylated sequence; when the tag sequence is designed as single-strand, the tag sequence is phosphorylated at its 5'-terminal so as to link to a sequence to be tested.

In one embodiment of the present invention, the fragmented sequences to be tested are end-filled and added with A so as to obtain sequences containing a protruded "A".

In one embodiment of the present invention, one tag sequence has a protruded "T" at 5'-terminal, so as to conveniently link to the sequence to be tested that carries the protruded "A".

In one embodiment of the present invention, the other tag sequence has one or more arbitrary bases at 3'-terminal to ensure linking direction. In the present invention, the determined bases and the random bases in the tag sequences are arranged in a mode of sequential arrangement (the determined bases are arranged in front of or behind the random bases) or mosaic arrangement, that is, the random bases are inserted in the determined bases.

In the present invention, when the tag sequence are designed, it should be avoided as much as possible that the tag sequences themselves form palindromic sequences, which would result in that the tag sequences cannot correctly link to the sequences to be tested; the designing methods for avoiding formation of palindromic sequences are well known in the art, for example, reverse complementary sequences should be avoided as much as possible when designing a tag sequence.

In the present invention, in order to avoid influences on accuracy of sequencing results or avoid complementary binding directly occurring between the tag sequences and the sequences to be tested, it should be avoided as much as possible during designing that the tag sequences have excessive identity to the reference sequences of the sequences to be tested; the first choice of the reference sequences should be known reference sequences of the genomic DNAs belonging to the same species of the sequences to be tested, and if there is no known reference sequence for the same species, known reference sequences of the genomic DNAs of similar species can be chosen; the methods for avoiding excessive identity are well known in the art, for example, the identity between the tag sequences and the reference sequences can be set as lower than 90%, for example, lower than 85%, lower than 80%, lower than 75%, lower than 70%, lower than 65%, lower than 60%, lower than 55%, lower than 50%.

In the present invention, the sequencing library refers to a group of DNA fragments for sequencing comprising the sequences to be tested and other sequences (e.g., sequencing adaptors).

In the present invention, the inserted fragments of the sequencing library refer to fragments comprising the sequences to be tested and tag sequences wherein other sequences such as sequencing adaptors are removed.

In the present invention, the sequence to be tested refer to a DNA fragment to be tested after treatment, the treatment comprising, for example, breaking, end filling, adding A, etc.

In one embodiment of the present invention, the sequence to be tested refer to the sequence to be sequenced that are obtained from the genomic DNA to be tested after breaking, end filing and adding A.

In the present invention, the equidirectional alternating concatemer formed by the sequence to be tested and tag sequence of the inserted fragment in the sequence library comprises two or more repetitive units (in which one sequence to be tested together with one tag sequence construct one repetitive unit). For example, if the sequence to be tested is A and the tag sequence is B, one repetitive unit can be A-B or B-A, and the equidirectional alternating concatemer comprises at least A-B-A-B or B-A-B-A; in addition, when there is a step of random breaking in construction of the sequencing library, the equidirectional alternating concatemer may have incomplete repetitive units, but comprises at least two or more repetitive units after splicing, for example, which can be 1/2A-B-A-B-A-B, or A-B-A-B-A-1/2B, or 1/2A-B-A-B-2/3A.

In the present invention, the DNA amplification based on strand displacement reaction (Roger S. Lasken, Genomic DNA amplification by the multiple displacement amplification (MDA) method. Biochemical Society Transactions, 2009, 37, 450-453) refers to DNA isothermal amplification in which when some DNA polymerases (e.g., including Phi 29 DNA polymerase, Bst DNA polymerase (large fragment)) meet downstream DNA strands in procedure of extending new strands, they can continue the extension reaction and split downstream double strands to generate free single strands. In general, the DNA amplification based on strand displacement reaction does not require thermal denaturation. Examples of the DNA amplification based on strand displacement reaction include strand displacement amplification, rolling circle amplification, multiple strand displacement amplification and ring-mediated amplification, etc.

In one embodiment of the present invention, multiple displacement amplification technique (also called multiple replacement amplification technical, MDA), which is an isothermal DNA amplification technique, is adopted, in which the strand displacement activity of Phi 29 DNA polymerase is used for massive amplification of DNA.

In another embodiment of the present invention, rolling circle amplification is used, in which circular DNA is used as a template, and massive amplification of circular DNA template is carried out by a strand displacement enzyme by using specific primers or random primers. After random primers are bound to single-strand circular DNA, phi29 DNA polymerase can perform synthesis of second strand along the circle; when synthesis is carried out to the initial position of primer, phi29 DNA polymerase with strand displacement activity opens the double strand at the location of the primer, so that new synthesis is carried out continuously. The newly synthesized DNA single strand can bind to new random hexamer primers for a new turn of synthesis. This cycle repeats to achieve effective amplification of circular DNA molecules.

In the present invention, a second-generation sequencing method refers to Sequencing by Synthesis, that is, a method of determining DNA sequence by capturing newly synthesized terminal tag, including but not limited to Roche/454 FLX, Illumina/Solexa Genome Analyzer and Applied Biosystems SOLID system.

In the present invention, a third-generation sequencing method refers to a single-molecule sequencing method, that is, each DNA molecule can be separately sequenced without PCR amplification during DNA sequencing, which includes but is not limited to single molecule fluorescence-based sequencing, and its representative technique is SMS technology of Helicos of USA, and SMART technology of Pacific Bioscience of USA, as well as nanopore sequencing.

In the present invention, for convenient discrimination, the tag sequences for preparing equidirectional alternating concatemer is called "tag sequences", while the tag sequences for sequencing is called "sequencing adaptors".

The sequencing library and uses thereof as provided in the present invention have at least the following beneficial effects:

1. For any sequencing depth, DNA amplification errors and sequencing errors can be removed effectively, so that mutations in DNA molecules can be determined ultra-accurately.

Tag sequences are linked to 5'-terminals of small DNA fragments to be sequenced (total length is less than half of sequencing length), then these chimeras are denatured to obtain single-strand linked fragment comprising the sequences to be tested and the tag sequences, followed with single-strand cyclization, the cyclized single-strand DNAs are subjected to rolling circle replication to construct equidirectional alternating concatemer comprising the sequences to be tested and the tag sequences. These repetitive units obtained by rolling circle replication are independent between each other during amplification procedure, so that errors generated respectively in each of these units during replication are also independent. The equidirectional alternating concatemer comprising the sequences to be tested and the tag sequences are used for construction of a sequencing library (fragments inserted in the library comprising at least two repetitive units). When this library is sequenced once, equidirectional repetitive units are tested at least twice, the sequences obtained by twice testing the repetitive units can be confirmed between each other, and those inconsistent bases revealed by twice testing the repetitive units are due to polymerase chain reaction errors or sequencing errors occurred during preparation of the library or sequencing procedure. The consistent sequence is the original sequence. Since the repetitive units to be sequenced are derived from circular DNA, tag sequences are needed to determine heads of sequences to be tested.

After a single strand DNA and its complementary strand are amplified, it cannot be determined from which strand the newly replicated DNA is derived, and this would disturb the identification of base error types. For example, mutation from C to T and mutation from G to A are two types of errors which are complementary in double-strand DNA, and thus, when the sequence is not labeled, it cannot be determined whether the mutation from C to T or the mutation from G to A occurs. Since tag sequences are of non-palindrome structure and linked to 5'-terminal of single-strand DNA, the original single-strand DNA can still be determined according to the direction of tag sequence, and thus the type of errors can be identified, which can help to identify infrequent mutations.

Due to imbalance of DNA amplification, some DNAs may have copy numbers significantly higher than average when a small amount of DNA is amplified to meet requirement of DNA sequencing. In the present invention, it is embodied as follows: an original single-strand DNA is subjected to rolling circle replication to obtain a plurality of sequences to be sequenced which together reflect information of the same original DNA, and thus there is a sequencing redundancy. However, in subsequent data processing, these sequences to be sequenced may be counted repeatedly since there is no information for determining whether these sequences are from the same original DNA single-strand ring. Therefore, this may bring about effects of error amplification: after a single-strand with DNA damage is subjected to single-strand rolling circle replication, it would exist in many sequences to be sequenced and be counted as a plurality of credible independent DNA mutations. Identification of such redundancy helps to exclude the above errors. In some embodiments of the present invention, tag sequences may comprise two parts: adaptor zone consisting of known bases and free zone consisting of random bases. The adaptor zone comprises 6 to 13 consecutive bases, and the free zone comprises 0 to 13 consecutive bases. It should be particularly pointed out that the free zone consists of random bases, and is designed as a certain length of 'N' (random bases) for synthesis of nucleotide sequence. The longer the length of the free zone, the higher the resolution of differentiation. If the free zone is designed to have a length of zero, the differentiation of sequences from different sources to be sequenced would depend on only: 1) different sizes of target DNA fragments deduced from the sequences to be sequenced; 2) different sequence compositions deduced from the target DNA fragments. The mechanism of the present invention is illustrated as follows by using a sequencing error rate of 1/100 (the second-generation sequencing has an error rate of 1/100 to 1/1000). The probability of concurrence of the same error at the same position of two repetitive units in a consensus sequence is $1/3*(1/100)^2$, i.e., error rate is $3*10^{-5}$ (the probability of error of consensus base for more repetitive units would be lower), and the probability that same error occurs in two different consensus sequence is $(1/3*(1/100)^2)^2$, i.e., $9*10^{-10}$. Thus, this method would effectively exclude errors occurred in construction of library and sequencing procedure, thereby achieving the goal of accurate sequencing.

2. Suitable for construction of sequencing libraries for trace short DNA fragments and even for single-strand DNA.

Because single-strand cyclization needs a small initial amount of DNA (nanograms or less) and short fragments (30-200 base-pairs), the amplification efficiency after cyclization is very high. Thus, it is particularly suitable for construction of sequencing libraries of seriously degraded DNAs such as free DNAs in peripheral blood or fossil DNAs.

3. Compatible with other methods such as target area trapping method (e.g., exon trapping, target gene trapping).

In the equidirectional alternating concatemer comprising the sequences to be tested and the tag sequences, as provided in the present invention, different copies from replication of original DNA are in series. When target area trapping is performed, the molecule trapped by probe comprises at least two equidirectional repetitive units, thereby capable of accurately determining DNA sequence.

4. The equidirectional alternating concatemer comprising the sequences to be tested and the tag sequences, as constructed by this method, can be used for construction of a plurality of second-generation sequencing libraries of short fragments, thereby suitable for various sequencing platforms.

BRIEF DESCRIPTION OF THE DRAWINGS

FIG. 1: shows ring sizes and distribution thereof after single-strand cyclization of Example 5 of the present invention.

SPECIFIC MODELS FOR CARRYING OUT THE INVENTION

The embodiments of the present invention are further illustrated as follows in conjunction with the examples, but those skilled in the art would understand that these examples are merely used for illustrating the present invention, rather than limiting the scope of the present invention. For those which specific conditions are not given in the examples, they would be carried out according to conventional conditions or conditions recommended by manufacturers. When reagents or instruments are not given manufacturers, they would be commercially available conventional products.

One of innovation points of the present invention lies in linking a tag sequence to a short fragment DNA molecule (total length of them is less than half of sequencing length of sequencer), performing single-strand cyclization, rolling circle replication, to obtain an equidirectional alternating concatemer of the sequence to be tested and the tag sequence, constructing sequencing library and sequencing. Specifically, it can be implemented by the following two schemes.

Scheme I:
Firstly, DNA is randomly broken into fragments with a length less than half of the sequencing read length of second-generation sequencer (the sum of the length after breaking and the length of a tag sequence should be less than half of the read length), then a tag sequence is linked, in which the first strand (positive strand) of the tag sequence is modified by phosphorylation at 5'-terminal, while a T base is protruded at 3'-terminal; the second strand (negative strand) is not subjected to modification of phosphorylation at 5'-terminal, while a G base is protruded at 3'-terminal. After high-temperature denaturation, the tag sequence at incision is removed, thus a DNA sequence containing single-strand tag sequence is formed, which is then subjected to high-temperature denaturation and immediate cooling so as to convert DNA into single strand. After being converted into single strand, the DNA containing tag sequence is cyclized by using single-strand cyclase. The cyclized DNA is amplified by rolling circle chain displacement based on random primers, so that the cyclized DNA molecule is amplified in a large amount. The resultant amplification product is an equidirectional alternating concatemer comprising target DNA molecule and tag sequence. Nucleotide sequence of the equidirectional alternating concatemer can be used for constructing a standard second-generation sequencing library (fragments inserted during construction of library should have a size greater than the sequencing length of a sequencer, so as to ensure that the resulted repetitive units are independent from each other).

Scheme II:
Firstly, DNA is randomly broken into fragments with a length less than half of the sequencing read length of a second-generation sequencer (the sum of the length after breaking and length of a tag sequence to be linked subsequently should also be less than half of the read length), then a specific tag sequence is linked thereto (same as Scheme I). After being converted into single strand, the DNA containing the tag sequence is cyclized by using a single-strand cyclase. The cyclized DNA is subjected to rolling circle amplification by using DNA polymerase (such as Phi29 DNA polymerase) with chain displacement function, in which the primer is the second strand (i.e., negative strand) in the tag sequence. After amplification, the first strand (i.e., positive strand) in the tag sequence is used as a primer to synthesize a duplex from the single-strand linear DNA after rolling. The double-strand DNA is composed of repetitive units comprising the tag sequence and the target DNA. After the double-strand DNA is purified, it can be used for constructing a standard second-generation sequencing library, in which fragments inserted during construction of library should have a size greater than the sequencing length of sequencer, so as to ensure the resultant repetitive units are independent from each other.

Example 1: Construction of Equidirectional Alternating Concatemer Library for Whole-Genome DNA Sequence to be Tested and Tag Sequence According to Scheme I (Illumina Platform)

1) DNA Fragmentation
Instruments and reagents:
Ultrasonic breaker: Covaris: S2 Focused-ultrasonicator
Breaking tube: Covaris Microtube 6×16 mm, catalog #: 520045
Agarose: Promega, Agarose, LE, Analytical Grade, catalog #: V3121
Power of electrophoresis apparatus: Beijing Liuyi Instrument Plant, DYY-7C type
Electrophoresis tank: Beijing Liuyi Instrument Plant, DYCP-31DN type electrophoresis tank
QIAGEN MinElute Gel Extraction Kit (250), Catalog #: 28606
Takara 20 bp DNA Ladder (Dye Plus), Takara Code, 3420A
Ultrasonic breaker (Covaris S2 Focused-ultrasonicator) was used to break 1 μg of purified PhiX 174 genome DNA into 150-200 bp (Intensity: 5, Duty Cycle: 10%, Cycles per Burst: 200, Temperature: 4° C., time: 60 s, number of cycles: 5), breaking system was in an amount of 50 μl.

4% agarose gel electrophoresis (80V, 70 min; 1×TAE), cutting gel and recovering (QIAGEN MinElute Gel Extraction Kit) 60-90 bp fragments (Takara 20 bp DNA Ladder), brief recovering steps: 6 times volume of buffer QG sol, adding with same volume of isopropanol, mixing homogeneously and then being separated by chromatography, eluted with buffer QG, eluted with buffer PE, dried by airing, eluted with 56 µl ddH$_2$O. See details in specification of QIAGEN MinElute Gel Extraction Kit.

2) End-Filling

Reagents: New England Biolabs: NEBNext® Ultra™ DNA Library Prep Kit for Illumina®, Catalog #: E7370S
Fragmented DNA: 55.5 µl
End Prep Enzyme Mix: 3 µl
End Repair Reaction Buffer (10×): 6.5 µl
In total: 65 µl
20° C. 30 min, 65° C. 30 min 3) Adding A at Terminal and Linking to Tag Sequence Reagents: New England Biolabs: NEBNext® Ultra™ DNA Library Prep Kit for Illumina®, Catalog #: E7370S
Filled DNA: 65 µl
Blunt/TA Ligase Master Mix: 15 µl
Ligation Enhancer: 1 µl
Tag sequence UO-A (50 pmol): 1 µl
ddH$_2$O: 1.5 µl
in total: 83.5 µl
20° C. 30 min, 65° C. 10 min, then immediately placed on ice for 3 min.

The product was purified with MinElute Reaction Cleanup Kit, eluted with 15 µl of double-distilled water.

Tag sequence: UO-A was obtained by annealing with mixture of 100 pmol UO-adaptor 1 (dissolved with annealing buffer solution: 10 mM Tris-HCl (pH 7.5), 1 mM EDTA, 0.1 mM NaCl) and 100 pmol UO-adaptor 2 (dissolved with annealing buffer solution: 10 mM Tris-HCl (pH 7.5), 1 mM EDTA, 0.1 mM NaCl) of same volume (94° C. 5 min, gradually cooling to 25° C. with a rate of 0.1° C. per second).

```
                                        (SEQ ID NO: 1)
UO-adaptor 1: 5'-pTATGGGCAGTCGT-3'

(SEQ ID NO: 2)
UO-adaptor 2: 5'-CGACTGCCCATAG-3'
```

Note: tag sequence included but was not limited to those formed with UO-adaptor 1 and UO-adaptor 2 in the example. Similarly hereinafter.

4) Single-Strand Cyclization

Instruments and reagents:
PCR apparatus: Eppendorf: Mastercycler pros
New England Biolabs: Exonuclease I (*E. coli*), Catalog #: M0293
New England Biolabs: Exonuclease III (*E. coli*), Catalog #: M0206
Epicentre: CircLigase II ssDNA Ligase, Catalog #: CL9025K The above fragmented DNA was dried by distillation at 37° C. to 4.2 µl.

95° C. 3 min (note: PCR apparatus should be capable of performing reaction of 100 µl system, otherwise, 4.2 µl would be dried out by distillation after 95° C. distillation), and immediately placed on ice for 3 min.

After completion, added with:
10× circligase buffer: 0.5 µl
10 mmol MnCl$_2$: 0.25 µl
Circligase (100 u/ul): 0.25 µl Cyclization was performed at 65° C. for 2 h, at 80° C. for 10 min.

After completion of cyclization, linear and dimer DNAs were digested:
Exonuclease I (*E. coli*): 0.25 µl
Exonuclease III (*E. coli*): 0.25 µl
37° C. 1 h, 80° C. 20 min.

5) Multiple Strand Displacement (MDA) Reaction

Whole-genome amplification (WGA) kit based on MDA mechanism was used for rolling circle amplification of the cyclized product.

Instruments and reagents:
PCR apparatus: Eppendorf: Mastercycler pros
GE healthcare: illustra GenomiPhi HY DNA Amplification Kits, Product code: 25-6600-20
Beckman Coulter, Inc: Agencourt AMPure XP, Item No. A63880
Took the above cyclized DNA: 2.5 µl
Sample buffer: 22.5 µl
95° C. 3 min, immediately placed on ice for 3 min.
After completion, added with:
Reaction buffer: 22.5 µl
Enzyme mix: 2.5 µl
In total 20 µl
30° C. 1 h, 65° C. 10 min.

The product was purified with Agencourt AMPure XP magnetic beads (Beckman Coulter, Inc). Briefly: the product after amplification was added with 1.8 times volume of magnetic beads, stood at room temperature for 5 min, absorbed with magnetic shelf for 5 min, subjected to removal of supernatant, washed with 70% alcohol twice, dried by airing, eluted with 50 µl buffer AE (10 mM Tris-Cl, 0.5 mM EDTA; pH 9.0). See details in the specification of the kit.

The purified product was the equidirectional alternating concatemer of the sequence to be tested and the tag sequence.

6) Constructing Illumina Library for Equidirectional Alternating Concatemer of Sequence to be Tested and Tag Sequence.

Commercially available kits for constructing standard Illumina libraries could be used, for example, TruSeq DNA Sample Preparation Kits, Nextera DNA Sample Preparation Kits. Specific steps comprised:

(1) DNA Fragmentation of Equidirectional Alternating Concatemer of Sequence to be Tested and Tag Sequence Instruments and reagents:
1) Ultrasonic breaker: Covaris: S2 Focused-ultrasonicator
2) Breaking tube: Covaris Microtube 6×16 mm, No.: 520045
3) Agarose: Promega, Agarose, LE, Analytical Grade, catalog 14: V3121

Ultrasonic breaker (Covaris S2 Focused-µltrasonicator) was used to break 2 µg of purified direct repeat concatemer of DNA fragments was broken into 500-700 bp (Intensity: 3, Duty Cycle: 5%, Cycles per Burst: 200, Temperature: 4° C., time: 15 s, number of cycles: 5), the breaking system was in an amount of 85 µl.

(2) End-Filling

Reagents: New England Biolabs: NEBNext® End Repair Module, Catalog #:E6050
QIAGEN: MinElute Reaction Cleanup Kit, Catalog #: 28206
Fragmented DNA: 85 µl
NEBNext End Repair Reaction Buffer: 10 µl
NEBNext End Repair Enzyme Mix: 5 µl In total: 100 µl
20° C. 30 min.
The product was purified with MinElute Reaction Cleanup Kit, and eluted with 43 µl ddH$_2$O.
(3) Adding A at Terminal
Reagents: New England Biolabs: NEBNext® dA-Tailing Module, Catalog #:E6053
QIAGEN: MinElute Reaction Cleanup Kit, Catalog #: 28206
Filled DNA: 42 µl
NEBNext dA-Tailing Reaction Buffer: 5 µl
Klenow Fragment (3'→5' exo-): 3 µl
In total: 50 µl
37° C. 30 min.
The product was purified with MinElute Reaction Cleanup Kit, and eluted with 35.5 µl ddH$_2$O.
(4) Linking Sequencing Adaptor Sequence
Reagents: Invitrogen: T4 DNA Ligase, Catalog #: 15224-041
DNA added with A at terminal: 34.5 µl
Adaptor sequence 1 (50 pmol): 3 µl
5×DNA ligase buffer: 10 µl
T4 DNA Ligase: 2.5 µl
In total: 50 µl
16° C. overnight (16 h).
2% Agarose gel electrophoresis (80V, 80 min; 1×TAE), cutting gel and recovering (QIAGEN MinElute Gel Extraction Kit) 500~700 bp fragments, eluting with 22 µl ddH$_2$O.
Adaptor Sequence 1:

```
Multiplexing Adaptor 1.0:
                                       (SEQ ID NO: 3)
5'-pGATCGGAAGAGCACACGTCT - 3'

Multiplexing Adaptor 2.0:
                                       (SEQ ID NO: 4)
5'- ACACTCTTTCCCTACACGACGCTCTTCCGATCT - 3'
```

Annealing adaptor sequences: taking 100 pmol Multiplexing Adapter 1.0 (dissolved with annealing buffer solution: 10 mM Tris-HCl (pH 7.5), 1 mM EDTA, 0.1 mM NaCl) and Multiplexing Adapter 2.0 (dissolved with annealing buffer solution: 10 mM Tris-HCl (pH 7.5), 1 mM EDTA, 0.1 mM NaCl) with same volume, 94° C. 5 min, then being gradually cooled to 25° C. at rate of 0.1° C. per second. After annealing, adaptor sequence with concentration of 50 pmol was obtained.
(5) PCR Amplification
Instruments:
PCR apparatus: Eppendorf: Mastercycler pros
Thermo scientific: Phusion High-Fidelity PCR Master Mix with HF Buffer, Catalog #: F531L
The above recovered DNA (about 30 ng)+ddH$_2$O: 23 µl
MP PCR primer 1.0 (10 pmol): 1 µl
MP index primer 1 (10 pmol): 1 µl
2× Phusion High-Fidelity PCR Master Mix: 25 µl
In total: 50 µl
PCR Amplification Circulation Conditions:
Pre-denaturation at 98° C. for 45 s, circulation amplification (98° C. 15 s, 65° C. 30 s, 72° C. 60 s) 10 times, 72° C. 5 min, 4° C. cooling.
2% Agarosegel electrophoresis (80V, 80 min; 1×TAE), cutting gel and recovering (QIAGEN MinElute Gel Extraction Kit) 500-700 bp fragments, eluting with 22 µl ddH$_2$O.
The eluted DNAs were a constructed library, and this library could be used for sequencing in second-generation sequencing platform.

Primer sequences were as follows:

```
MP PCR primer 1.0:
                                       (SEQ ID NO: 5)
5'-AATGATACGGCGACCACCGAGATCTACACTCTTTCCCTACACGAC

GCTCTTCCGATCT - 3'

MP index primer 1:
                                       (SEQ ID NO: 6)
5'-CAAGCAGAAGACGGCATACGAGATCGTGATGTGACTGGAGTTCAGAC

GTGTGCTCTTCCGATCT -3'
```

Example 2: Construction of Equidirectional Alternating Concatemer Library for Human Exon Sequence to be Tested and Tag Sequence According to Scheme I (Illumina Sequencing Platform)

1) DNA Fragmentation
The used instruments and reagents were as those of Example 1. Ultrasonic breaker was used to break 1 µg of purified human peripheral blood genome DNA into 300 bp (Intensity: 4, Duty Cycle: 10%, Cycles per Burst: 200, Temperature: 4° C., time: 60 s, number of cycles: 2), the breaking system was in an amount of 50 µl.
4% Agarose gel electrophoresis (80V, 70 min; 1×TAE), cutting gel and recovering 80~130 bp fragments, brief recovering steps: 6 times volume of buffer QG sol, adding with same volume of isopropanol, mixing and being separated by chromatography, eluted with buffer QG, eluted with buffer PE, dried by airing, eluted with 56 µl ddH$_2$O. See details in specification of QIAGEN MinElute Gel Extraction Kit.
2) End-Filling
Reagents: see also those in Example 1.
Fragmented DNA of step 1): 55.5 µl
End Prep Enzyme Mix: 3 µl
End Repair Reaction Buffer (10×): 6.5 µl
In total: 65 µl
20° C. 30 min, 65° C. 30 min.
3) Adding A at Terminal and Linking to Tag Sequence
Reagents: see also those in Example 1.
Filled DNA of step 2): 65 µl
Blunt/TA Ligase Master Mix: 15 µl
Ligation Enhancer: 1 µl
tag sequence UO-A (50 pmol): 1 µl
ddH$_2$O: 1.5 µl
In total: 83.5 µl
20° C. 30 min, 65° C. 10 min, then immediately placed on ice for 3 min.
The product was purified with MinElute Reaction Cleanup Kit, eluted with 15 µl ddH$_2$O.
Tag sequence: UO-A was obtained by annealing with mixture of 100 pmol UO-adaptor 1 (dissolved in annealing buffer solution: 10 mM Tris-HCl (pH 7.5), 1 mM EDTA, 0.1 mM NaCl) and 100 pmol UO-adaptor 2 (dissolved in annealing buffer solution: 10 mM Tris-HCl (pH 7.5), 1 mM EDTA, 0.1 mM NaCl) of same volume (94° C. 5 min, gradually cooling to 25° C. with a rate of 0.1° C. per second).

```
UO-adaptor 1: 5' - pTATGGGCAGTCGT - 3'

UO-adaptor 2: 5' - CGACTGCCCATAG - 3'
```

4) Single-Strand Cyclization of DNA

Instruments and reagents: see those in Example 1.

The fragmented DNA of step 3) was dried by distillation at 37° C. to reach 4.2 μl.

95° C. 3 min (note: PCR apparatus should be capable of performing reaction of 100 μl system, otherwise, 4.2 μl would be dried out after 95° C. distillation), and immediately placed on ice for 3 min;

After completion, added with:
10× circligase buffer: 0.5 μl
10 mmol Mncl 2: 0.25 μl
Circligase (100 u/μl): 0.25 μl
65° C. 2 h, 80° C. 10 min;

After completion of cyclization, linear and dimer DNAs were digested:
Exonuclease I (E. coli): 0.25 μl
Exonuclease III (E. coli): 0.25 μl
37° C. 1 h, 80° C. 20 min.

5) Multiple Strand Displacement (MDA) Reaction

Whole-genome amplification (WGA) kit based on MDA mechanism was used for rolling circle amplification of the cyclized product.

Instruments and reagents: see those in Example 1.
The above cyclized DNA: 2.5 μl
Sample buffer: 22.5 μl
95° C. 3 min, immediately placed on ice for 3 min;
After completion, added with:
Reaction buffer: 22.5 μl
Enzyme mix: 2.5 μl
In total 20 μl
30° C. 1 h, 65° C. 10 min;

The product was purified with Agencourt AMPure XP magnetic beads (Beckman Coulter, Inc). Briefly: the product after amplification was added with 1.8 times volume of magnetic beads, stood at room temperature for 5 min, absorbed with magnetic shelf for 5 min, subjected to removal of supernatant, washed with 70% alcohol twice, dried by airing, eluted with 50 μl buffer AE (10 mM Tris-Cl, 0.5 mM EDTA; pH 9.0). See details in the specification of the kit.

The purified product was the equidirectional alternating concatemer of the sequence to be tested and the tag sequence.

6) Constructing Exon Trapping Library (Illumina Sequencing Platform) for the Above Prepared Equidirectional Alternating Concatemer of Sequence to be Tested and Tag Sequence.

Commercially available kits for constructing exon trapping libraries could be used, for example, Agilent: SureSelect Human All Exon Kits.

(1) DNA Fragmentation of Equidirectional Alternating Concatemer of Sequence to be Tested and Tag Sequence Instruments and reagents: see those in Example 1.

Ultrasonic breaker was used to break 2 μg of the purified equidirectional alternating concatemer of sequence to be tested and tag sequence into 500-700 bp (Intensity: 3, Duty Cycle: 5%, Cycles per Burst: 200, Temperature: 4° C., time: 15 s, number of cycles: 5), the breaking system was in an amount of 85 μl.

(2) End-Filling

Reagents: see those in Example 1.
Fragmented DNA of step (1): 85 μl
NEBNext End Repair Reaction Buffer: 10 μl
NEBNext End Repair Enzyme Mix: 5 μl
In total: 100 μl
20° C. 30 min;

The product was purified with MinElute Reaction Cleanup Kit, and eluted with 43 μl ddH$_2$O.

(3) Adding A at Terminal

Reagents: see those in Example 1.
Filled DNA of step (2): 42 μl
NEBNext dA-Tailing Reaction Buffer: 5 μl
Klenow Fragment (3'→5' exo-): 3 μl
In total: 50 μl
37° C. 30 min;

The product was purified with MinElute Reaction Cleanup Kit, eluted with 35.5 μl ddH$_2$O.

(4) Linking Sequencing Adaptor Sequence

Reagents: see those in Example 1.
DNA added with A at terminal: 34.5 μl
Adaptor sequence 1 (50 pmol): 3 μl
5×DNA ligase buffer: 10 μl
T4 DNA Ligase: 2.5 μl
In total: 50 μl
16° C. overnight (16 h);

2% Agarose gel electrophoresis (80V, 80 min; 1×TAE), cutting gel and recovering (QIAGEN MinElute Gel Extraction Kit) 500-700 bp fragments, eluting with 22 μl ddH$_2$O.

Adaptor Sequence 1:

```
Multiplexing Adaptor 1.0:
5'- pGATCGGAAGAGCACACGTCT - 3'

Multiplexing Adaptor 2.0:
5'- ACACTCTTTCCCTACACGACGCTCTTCCGATCT - 3'
```

Annealing adaptor sequences: taking 100 pmol Multiplexing Adapter 1.0 (dissolved with annealing buffer solution: 10 mM Tris-HCl (pH 7.5), 1 mM EDTA, 0.1 mM NaCl) and Multiplexing Adapter 2.0 (dissolved with annealing buffer solution: 10 mM Tris-HCl (pH 7.5), 1 mM EDTA, 0.1 mM NaCl) with same volume, 94° C. 5 min, then being gradually cooled to 25° C. with a rate of 0.1° C. per second. After annealing, adaptor sequence 1 with concentration of 50 pmol was obtained.

(5) PCR Amplification

Instruments and reagents:
PCR apparatus: Eppendorf: Mastecycler pro s
Agilent: Herculase II Fusion DNA Polymerases, Catalog #: 600677
QIAGEN: MinElute Reaction Cleanup Kit, Catalog #: 28206

Four reactions were performed in parallel model, and each of the reactions had following formula:
The above recovered DNA (about 90 ng)+ddH$_2$O: 36.5 μl
MP PCR primer 1.0 (10 pmol): 1 μl
MP index primer 1 (10 pmol): 1 μl
5× Herculase II Reaction Buffer: 10 μl
dNTPs (100 mM; 25 mM each dNTP): 0.5 μl
Herculase H Fusion DNA Polymerase: 1 μl
In total: 50 μl PCR amplification circulation conditions:
Pre-denaturation at 98° C. for 2 min, circulation amplification (98° C. 30 s, 65° C. 30 s, 72° C. 30 s) 8 times, 72° C. 10 min, 4° C. cooling.

After completion of PCR, the PCR products in 4 reaction tubes were concentrated (MinElute Reaction Cleanup Kit), eluted with 46 μl ddH2O.

2% Agarose gel electrophoresis (80V, 90 min; 1×TAE), cutting gel and recovering (QIAGEN MinElute Gel Extraction Kit) 500~700 bp fragments, eluted with 26 μl ddH2O.

Primer sequences were as follows:

```
MP PCR primer 1.0:
5'-AATGATACGGCGACCACCGAGATCTACACTCTTTCCCTACACGACGC

TCTTCCGATCT - 3'

MP index primer 1:
5'-CAAGCAGAAGACGGCATACGAGATCGTGATGTGACTGGAGTTCAGAC

GTGTGCTCTTCCGATCT - 3'
```

(6) Exon Probe Hybridization

In the present test, Agilent: SureSelect Human All Exon Kits was used to perform exon probe hybridization for the above PCR reaction product. Briefly:

Preparing hybridization buffer solution:
SureSelect Hyb #1 (orange cap, or bottle): 25 μl
SureSelect Hyb #2 (red cap): 1 μl
SureSelect Hyb #3 (yellow cap): 10 μl
SureSelect Hyb #4 (black cap, or bottle): 13 μl
In total: 49 μl
65° C. 5 min.
Preparing trapping library mixture:
SureSelect Library: 5 μl
SureSelect RNase Block (purple cap): 0.5 μl
ddH₂O: 1.5 μl
In total: 7 μl
65° C. 2 min.
Preparing sample mixture:
Purified DNA (about 700 ng): 3.4 μl
SureSelect Indexing Block #1 (green cap): 2.5 μl
SureSelect Block #2 (blue cap): 2.5 μl
SureSelect Indexing Block #3 (brown cap): 0.6 μl
In total: 9 μl
95° C. 5 min, 65° C. hold.

13 μl of the prepared hybridization buffer solution was added with the trapping library mixture (7 μl), then added with the sample mixture (9 μl), in total 29 μl, hybridized at 65° C. for 24 h.

Magnetic beads (Invitrogen™: Dynabeads® M-280 Streptavidin, Catalog #: 11205D) were used to trap the hybridized fragments (50 μl of magnetic beads, washed with 200 μl SureSelect Binding Buffer for 3 times, the magnetic beads were resuspended in 200 μl SureSelect Binding Buffer, added with the hybridization product, stood at room temperature for 30 min, absorbed with magnetic beads, washed with SureSelect Wash 1 once, washed with SureSelect Wash 2 for 3 times, the magnetic beads were resuspended in 36.5 μl ddH₂O), see details in operation manual of Agilent: SureSelect Human All Exon Kits.

(7) PCR after Probe Hybridization

Instruments and reagents:
PCR apparatus: Eppendorf: Mastecycler pro s
Agilent: Herculase II Fusion DNA Polymerases, Catalog #: 600677
Beckman Coulter, Inc: Agencourt AMPure XP, Item No. A63880

Four reactions were performed in parallel model, and each of the reactions had reaction formula as follows:

Magnetic beads resuspended during exon probe hybridization: 36.5 μl
MP PCR primer 1.0 (10 pmol): 1 μl
MP PCR primer 2.0 (10 pmol): 1 μl
5× Herculase II Reaction Buffer: 10 μl
dNTPs (100 mM; 25 mM each dNTP): 0.5 μl
Herculase II Fusion DNA Polymerase: 1 μl
In total: 50 μl.

PCR amplification circulation conditions:
Pre-denaturation at 98° C. for 2 min, circulation amplification (98° C. 30 s, 65° C. 30 s, 72° C. 30 s) 12 times, 72° C. 10 min, 4° C. cooling.

Primer sequences were as follows:

```
MP PCR primer 1.0:
5'-AATGATACGGCGACCACCGAGATCTACACTCTTTCCCTACACGACGC

TCTTCCGATCT - 3'

MP PCR primer 2.0:
                                        (SEQ ID NO: 7)
5'- CAAGCAGAAGACGGCATACGAGAT - 3'
```

After completion of PCR, Agencourt AMPure XP magnetic beads were used for purification, briefly: the amplification product was added with 1.8 times volume of magnetic beads, stood at room temperature for 5 min, absorbed with magnetic shelf for 5 min, subjected to removal of supernatant, washed with 70% alcohol twice, dried by airing, eluted with 16 μl ddH₂O. See details in the specification of the kit.

The eluted DNA was equidirectional alternating concatemer library of the constructed human exon sequence to be tested and the tag sequence, and the library could be used for sequencing in second-generation sequencing platform.

Example 3: Construction of Equidirectional Alternating Concatemer Library for Peripheral Blood Free DNA Sequence to be Tested and Tag Sequence According to Scheme I (Illumina Sequencing Platform)

1) Extracting Peripheral Blood Free DNA and Determining Fragment Size Thereof

Instruments and reagents:
QIAGEN: QIAamp Circulating Nucleic Acid Kit, catalog #: 55114
Agilent: 2100 bioanalyzer 2 ml of blood plasma was collected, QIAamp Circulating Nucleic Acid Kit of QIAGEN was used to extract DNA (cell-free circulating DNA) in the plasma, and elution was performed by using 20 μl ddH₂O (the extraction method could be seen in the specification of the kit). 2100 bioanalyzer of Agilent was used to determine the size distribution of the extracted fragments. It could be seen in the results that the free DNA fragments of normal human subjects had a size centered around 172 bp, a distribution range of about (130 bp-230 bp), and a concentration of 0.354 ng/μl, while the free DNA fragments of patients with liver cancer had a size centered around 164 bp, a distribution range of about (110 bp-210 bp), and a concentration of 4.78 ng/μl.

2) End-Filling
Reagents: see those in Example 1.
Extracted-peripheral blood free DNA (50 ng)+ddH2O: 55.5 μl
End Prep Enzyme Mix: 3 μl
End Repair Reaction Buffer (10×): 6.5 μl
In total: 65 μl
20° C. 30 min, 65° C. 30 min.

3) Adding A at Terminal and Linking to Tag Sequence
Reagents: see those in Example 1
Filled DNA: 65 μl
Blunt/TA Ligase Master Mix: 15 μl
Ligation Enhancer: 1 μl
Tag sequence UO-A (50 pmol): 1 μl
ddH₂O: 1.5 μl
In total: 83.5 μl 20° C. 30 min, 65° C. 10 min, immediately placed on ice for 3 min.

The product was purified with MinElute Reaction Cleanup Kit, eluted with 15 μl ddH2O.

Tag sequence: UO-A was obtained by annealing with mixture of 100 pmol UO-adaptor 1 (dissolved in annealing buffer solution: 10 mM Tris-HCl (pH 7.5), 1 mM EDTA, 0.1 mM NaCl) and 100 pmol UO-adaptor 2 (dissolved in annealing buffer solution: 10 mM Tris-HCl (pH 7.5), 1 mM EDTA, 0.1 mM NaCl) of same volume (94° C. 5 min, gradually cooling to 25° C. with a rate of 0.1° C. per second).

```
UO-adaptor1: 5'- pTATGGGCAGTCGT - 3'

UO-adaptor2: 5'- CGACTGCCCATAG - 3'
```

4) Single-Strand Cyclization of DNA

Instruments and reagents: see those in Example 1.

The extracted-peripheral blood free DNA was dried by distillation at 37° C. to reach 4.2 μl.

95° C. 3 min (note: PCR apparatus should be capable of performing reaction of 100 μl system, otherwise, 4.2 μl would be dried out after 95° C. distillation), and immediately placed on ice for 3 min;

After completion, added with:
10× circligase buffer: 0.5 μl
10 mmol MnCl$_2$: 0.25 μl
Circligase (100 u/μl): 0.25 μl
65° C. 2 h, 80° C. 10 min.

After completion of cyclization, linear and dimer DNAs were digested:
Exonuclease I (*E. coli*): 0.25 μl
Exonuclease III (*E. coli*): 0.25 μl
37° C. 1 h, 80° C. 20 min.

5) Multiple Strand Displacement (MDA) Reaction

Whole-genome amplification (WGA) kit based on MDA mechanism was used for rolling circle amplification of the cyclized product.

Instruments and reagents: see those in Example 1.
The above cyclized DNA: 2.5 μl
Sample buffer: 22.5 μl
95° C. 3 min, immediately placed on ice for 3 min;
After completion, added with:
Reaction buffer: 22.5 μl Enzyme mix: 2.5 μl
In total: 20 μl
30° C. 1 h, 65° C. 10 min.

The product was purified with Agencourt AMPure XP magnetic beads (Beckman Coulter, Inc). Briefly: the product after amplification was added with 1.8 times volume of magnetic beads, stood at room temperature for 5 min, absorbed with magnetic shelf for 5 min, subjected to removal of supernatant, washed with 70% alcohol twice, dried by airing, eluted with 50 μl buffer AE (10 mM Tris-Cl, 0.5 mM EDTA; pH 9.0). See details in the specification of the kit.

The purified product was the equidirectional alternating concatemer of the sequence to be tested and the tag sequence.

6) Constructing Illumina Sequencing Library for the Above Prepared Equidirectional Alternating Concatemer of Sequence to be Tested and Tag Sequence.

Commercially available kits for constructing standard Illumian libraries could be used, for example, TruSeq DNA Sample Preparation Kits, Nextera DNA Sample Preparation Kits.

(1) DNA Fragmentation of Direct Repeat Concatemer

Instruments and reagents: see those in Example 1.

Ultrasonic breaker was used to break 2 μg of the purified equidirectional alternating concatemer of sequence to be tested and tag sequence into 500-700 bp (Intensity: 3, Duty Cycle: 5%, Cycles per Burst: 200, Temperature: 4° C., time: 15 s, number of cycles: 5), the breaking system was in an amount of 85 μl.

(2) End-Filling

Reagents: see those in Example 1.
Fragmented DNA: 85 μl
NEBNext End Repair Reaction Buffer: 10 μl
NEBNext End Repair Enzyme Mix: 5 μl
In total: 100 μl
20° C. 30 min;

The product was purified with MinElute Reaction Cleanup Kit, and eluted with 43 μl ddH2O.

(3) Adding A at Terminal

Reagents: see those in Example 1.
Filled DNA: 42 μl
NEBNext dA-Tailing Reaction Buffer: 5 μl
Klenow Fragment (3'→5' exo-): 3 μl
In total: 50 μl
37° C. 30 min;

The product was purified with MinElute Reaction Cleanup Kit, and eluted with 35.5 μl ddH2O.

(4) Linking Sequencing Adaptor Sequence

Reagents: see those in Example 1.
DNA added with A at terminal: 34.5 μl
Adaptor sequence 1 (50 pmol): 3 μl
5×DNA ligase buffer: 10 μl
T4 DNA Ligase: 2.5 μl
In total: 50 μl 16° C. overnight (16 h).

2% Agarose gel electrophoresis (80V, 80 min; 1×TAE), cutting gel and recovering (QIAGEN MinElute Gel Extraction Kit) 500-700 bp fragments, eluting with 22 μl ddH2O.

Adaptor Sequence 1:

```
Multiplexing Adaptor 1.0:
5'- pGATCGGAAGAGCACACGTCT - 3'

Multiplexing Adaptor 2.0:
5'- ACACTCTTTCCCTACACGACGCTCTTCCGATCT - 3'
```

Annealing adaptor sequences: taking 100 pmol Multiplexing Adapter 1.0 (dissolved with annealing buffer solution: 10 mM Tris-HCl (pH 7.5), 1 mM EDTA, 0.1 mM NaCl) and Multiplexing Adapter 2.0 (dissolved with annealing buffer solution: 10 mM Tris-HCl (pH 7.5), 1 mM EDTA, 0.1 mM NaCl) with same volume, 94° C. 5 min, then being gradually cooled to 25° C. with a rate of 0.1° C. per second. After annealing, adaptor sequence 1 with concentration of 50 pmol was obtained.

(5) PCR Amplification

Instruments and reagents: see those in Example 1.
The above recovered DNA (about 30 ng)+ddH$_2$O: 23 μl
MP PCR primer 1.0 (10 pmol): 1 μl
MP index primer 1 (10 pmol): 1 μl
2× Phusion High-Fidelity PCR Master Mix: 25 μl
In total: 50 μl.

PCR amplification circulation conditions:
Pre-denaturation at 98° C. for 45 s, circulation amplification (98° C. 15 s, 65° C. 30 s, 72° C. 60 s) 10 times, 72° C. 5 min, 4° C. cooling.

2% Agarose gel electrophoresis (80V, 80 min; 1×TAE), cutting gel and recovering (QIAGEN MinElute Gel Extraction Kit) 500-700 bp fragments, eluting with 22 μl ddH$_2$O.

The eluted DNAs were the constructed library, and this library could be used for sequencing in second-generation sequencing platform.

Primer sequences were as follows:

```
MP PCR primer 1.0:
5'-AATGATACGGCGACCACCGAGATCTACACTCTTTCCCTACACGACGC

TCTTCCGATCT - 3'

MP index primer 1:
5'-CAAGCAGAAGACGGCATACGAGATCGTGATGTGACTGGAGTTCAGAC

GTGTGCTCTTCCGATCT - 3'
```

Example 4: Construction of Equidirectional Alternating Concatemer Library for Sequence to be Tested and Tag Sequence According to Scheme II (Illumina Sequencing Platform)

Steps:
1) DNA Fragmentation
Instruments and reagents: see those in Example 1.
Ultrasonic breaker was used to break 1 µg of the purified *Drosophila melanogaster* genome DNA into 150-200 bp (Intensity: 5, Duty Cycle: 10%, Cycles per Burst: 200, Temperature: 4° C., time: 60 s, number of cycles: 5), the breaking system was in an amount of 50 µl.

4% agarose gel electrophoresis (80V, 70 min; 1×TAE), cutting gel and recovering 60-90 bp fragments, brief recovering steps: 6 times volume of buffer QG sol, adding with same volume of isopropanol, mixing homogeneously and then being separated by chromatography, eluted with buffer QG, eluted with buffer PE, dried by airing, eluted with 56 µl ddH$_2$O. See details in specification of QIAGEN MinElute Gel Extraction Kit.

2) End-Filling
Reagents: see those in Example 1.
Fragmented DNA: 55.5 µl
End Prep Enzyme Mix: 3 µl
End Repair Reaction Buffer (10λ): 6.5 µl
In total: 65 µl
20° C. 30 min, 65° C. 30 min.

3) Adding A at Terminal and Linking to Tag Sequence
Reagents: see those in Example 1.
Filled DNA: 65 µl
Blunt/TA Ligase Master Mix: 15 µl
Ligation Enhancer: 1 µl
tag sequence UO-A (50 pmol): 1 µl
ddH2O: 1.5 µl
In total: 83.5 µl
20° C. 30 min, 65° C. 10 min, immediately placed on ice for 3 min.

The product was purified with MinElute Reaction Cleanup Kit, and eluted with 15 µl ddH$_2$O.

Tag sequence: UO-A was obtained by annealing with mixture of 100 pmol UO-adaptor 1 (dissolved with annealing buffer solution: 10 mM Tris-HCl (pH 7.5), 1 mM EDTA, 0.1 mM NaCl) and 100 pmol UO-adaptor 2 (dissolved with annealing buffer solution: 10 mM Tris-HCl (pH 7.5), 1 mM EDTA, 0.1 mM NaCl) of same volume (94° C. 5 min, gradually cooling to 25° C. with a rate of 0.1° C. per second).

```
UO-adaptor1: 5' - pTATGGGCAGTCGT - 3'

UO-adaptor2: 5' - CGACTGCCCATAG - 3'
```

4) Single-Strand Cyclization of DNA
Instruments and reagents: see those in Example 1.
The above fragmented DNA was dried by distillation at 37° C. to 4.2 µl.
95° C. 3 min (note: PCR apparatus should be capable of performing reaction of 100 µl system, otherwise, 4.2 µl would be dried out by distillation after 95° C. distillation), and immediately placed on ice for 3 min.
After completion, added with:
10× circligase buffer: 0.5 µl
10 mmol MnCl$_2$: 0.25 µl
Circligase (100 u/µl): 0.25 µl
65° C. 2 h, 80° C. 10 min;
After completion of cyclization, linear and dimer DNAs were digested:
Exonuclease I (*E. coli*): 0.25 µl
Exonuclease III (*E. coli*): 0.25 µl
37° C. 1 h, 80° C. 20 min.

5) Rolling Circle Amplification
Instruments and reagents:
PCR apparatus: Eppendorf: Mastecycler pros
New England Biolabs: phi29 DNA Polymerase, Catalog #: M0269L
Single-strand cyclized DNA: 5.7 µl
Phi29 DNA Polymerase Reaction Buffer: 2 µl
Primer UO-a3 (10 pmol): 1 µl
ddH$_2$O: 8.9 µl
In total: 17.6 µl, 95° C. 3 min, immediately placed on ice for 3 min.
After completion, added with:
10 mM dNTP: 1 µl
100×BSA: 0.4 µl
phi29 DNA Polymerase (10 U/µl): 1 µl
In total: 20 µl
30° C. 8 h, 65° C. 10 min.

```
Primer sequence: UO-a3:
                             (SEQ ID NO: 8)
           5' - ACGACTGCCCATAT - 3'
```

6) Converting Linear DNA into Double Strand
Instruments and reagents:
PCR apparatus: Eppendorf: Mastecycler pros
New England Biolabs: phi29 DNA Polymerase, Catalog #: M0269L
New England Biolabs: Exonuclease I (*E. coli*), Catalog #: M0293
New England Biolabs: T4 DNA polymerase, Catalog #: m0203
Epicentre: Ampligase® Enzyme and Buffer, Catalog #:A3202K
Beckman Coulter, Inc: Agencourt AMPure XP, Item No. A63880
Rolling circle amplified DNA: 20 µl
Primer UO-a1 (10p): 1 µl
Ampligase 10× Reaction Buffer: 5 µl
2.5 mM dNTP: 1 µl
ddH$_2$O: 22.5 µl
95° C. 3 min, immediately placed on ice for 3 min,
After completion, added with:
T4 DNA polymerase: 0.5 µl
12° C. 2.5 h, 75° C. 20 min.

After completion, added with:
Ampligase DNA Ligase: 3 μl
60° C. 1 h.
After completion, added with:
Exonuclease I: 1 μl
37° C. 1 h, 80° C. 20 min.

The product was purified with Agencourt AMPure XP magnetic beads. Briefly: the product after amplification was added with 1.8 times volume of magnetic beads, stood at room temperature for 5 min, absorbed with magnetic shelf for 5 min, subjected to removal of supernatant, washed with 70% alcohol twice, dried by airing, eluted with 20 μl ddH$_2$O. See details in the specification of the kit.

The purified product was a direct repeat concatemer of the DNA fragment.

```
Primer sequence UO-a1: 5'-pTATGGGCAGTCGT-3'
```

7) Constructing Illumina Sequencing Library for the Above Prepared Equidirectional Alternating Concatemer of Sequence to be Tested and Tag Sequence.

After rolling circle amplification for 8 h, the obtained DNA had an amount ranging from dozens of nanograms to hundreds of nanograms, and the yield of DNA after rolling circle amplification could be elevated by increasing time of rolling circle amplification. According to the obtained DNA amount, a suitable commercially available kit could be chosen to construct standard Illumina library: if DNA in an amount of dozens of nanograms was obtained, Nextera DNA Sample Preparation Kits or other kits for constructing libraries based on small amount of DNA could be used; if DNA in an amount of hundreds of nanograms was obtained, TruSeq DNA Sample Preparation Kits or other kits for large initial amount of DNA could be used.

This test used a method for constructing libraries based on transposase EZ-Tn5:

(1) Assembling Transposons
Epi_MA1 (10 pmol): 1 μl
Epi_MA2 (10 pmol): 1 μl
Glycerol: 0.5 μl
1 U/μl transposase EZ-Tn5 (epicentre): 2.5 μl
In total: 5 μl
25° C. 20 min.

(2) DNA Fragmentation
The above transposons: 5 μl
5×LMW buffer: 2 μl
The above obtained direct repeat concatemer DNA (about 30 ng)+ddH2O: 3 μl
In total: 10 μl
55° C. 10 min.

The product was purified with MinElute Reaction Cleanup Kit, eluted with 24 μl ddH2O.

(3) PCR Amplification of the Recovered Product
Instruments and reagents: see those in Example 1.
The above recovered DNA (about 30 ng)+ddH2O: 23 μl
Epi_PCR primer 1.0 (10 pmol): 1 μl
Epi_index primer (10 pmol): 1 μl
2× Phusion High-Fidelity PCR Master Mix: 25 μl
In total: 50 μl PCR amplification circulation conditions:
72° C. 3 min (imperative), 98° C. 30 s, circulation amplification (98° C. 10 s, 65° C. 30 s, 72° C. 3 min) 10 times, 4° C. cooling.

2% Agarose gel electrophoresis (80V, 80 min; 1×TAE), cutting gel and recovering (QIAGEN MinElute Gel Extraction Kit) 500~800 bp fragments, eluted with 17 μl ddH2O.

The eluted DNA was the constructed library, and this library could be used for sequencing in second-generation sequencing platform.

The above primer sequences were as follows:

```
Epi_ME:
                                           (SEQ ID NO: 9)
5'- CTGTCTCTTATACACATCT - 3'

Epi_Adaptor1:
                                           (SEQ ID NO: 10)
5'- CTACACGCCTCCCTCGCGCCATCAGAGATGTGTATAAGAGACAG -
3'

Epi_Adaptor2:
                                           (SEQ ID NO: 11)
5'- CGGTCTGCCTTGCCAGCCCGCTCAGAGATGTGTATAAGAGACAG -
3'

Epi_PCR primer 1.0:
                                           (SEQ ID NO: 12)
5'- AATGATACGGCGACCACCGAGATCTACACGCCTCCCTCGCGCCATC
AG - 3'

Epi_PCR index primer:
                                           (SEQ ID NO: 13)
5'- CAAGCAGAAGACGGCATACGAGATCGTGATCGGTCTGCCTTGCCAG
CCCGCTCAG - 3'
```

Epi_MA1: Obtained by annealing with 100 pmol Epi_ME (dissolved in annealing buffer solution: 10 mM Tris-HCl (pH 7.5), 1 mM EDTA, 0.1 mM NaCl) and Epi_Adaptor 1 (dissolved in annealing buffer solution: 10 mM Tris-HCl (pH 7.5), 1 mM EDTA, 0.1 NaCl) with same volume. Conditions: 94° C. 5 min, following with gradually cooling to 25° C. with a rate of 0.1° C. per second.

Epi_MA2: Obtained by annealing with 100 pmol Epi_ME (dissolved in annealing buffer solution: 10 mM Tris-HCl (pH 7.5), 1 mM EDTA, 0.1 mM NaCl) and Epi_Adaptor 2 (dissolved in annealing buffer solution: 10 mM Tris-HCl (pH 7.5), 1 mM EDTA, 0.1 mM NaCl) with same volume. Conditions: 94° C. 5 min, following with gradually cooling to 25° C. with a rate of 0.1° C. per second.

5×LMW buffer: 50 mM Tris-OAc, pH 8.0, 25 mM Mg(OAc)$_2$

Constructing Oseq library according to Example 1.

Example 5: Library Construction and Data Analysis for Phage Phix174

1 μg of phage Phix174 DNA was ultrasonically broken into 300 bp DNA fragments. 60~80 bp fragments were recovered, linked to tag sequence, converted into single strand, and subjected to rolling circle amplification (see details in Example 1). The DNA after rolling circle amplification was subjected to second-generation sequencing library construction based on transposons (see details in Example 4). About 10G of bi-directional data (read length was 2×100=200 bp) were obtained by using hiseq 2000. The data were treated and analyzed as follows:

1. Measured in total: 54391601 reads, in which the number of reads capable of forming rings (at least two repetitive units could be detected, similarly hereinafter) was: 33987941 reads.

2. Cyclization rate: OS2_in2: (135951764/4)/(217566404/4)=62.49%

3. For the formed rings, size range was: 30-162 bp, average size was: 72.5333 bp, standard deviation was: 14.06478, median was: 71 bp. Specific distribution was shown in FIG. 1.

4. The constructed library of the equidirectional alternating concatemer of sequence to be tested and tag sequence was subjected to high-throughput Pair-End sequencing. Because the ring size was less than half of the sequencing length of sequencer, the concatemer of at least one unit must be covered by single-end sequencing once, the concatemer units must be tested twice by pair-end sequencing once, and inconsistent sequences could be removed by comparing the two concatemer sequences. By using this principle, the error rate of DNA in the measured data was calculated. If there is not infrequent mutation in sample, this method would have an error rate of 1e-5. Sequencing errors had different distributions on different bases (referring to bases of genome), in which sequencing error rates from C to T and G to A were relatively high, i.e., about 1e-4, and specific sequencing error rates were shown in Table 1. This kind of mutation pattern was also found in other researches for determining infrequent mutations, and these two kinds of mutations were likely caused by spontaneous deamination of cytosine or 5-methylated cytosine. After deamination, bases of one original single strand DNA changed, and only mutated bases could be observed in a plurality of independent determinations.

TABLE 1

Sequencing error rates of different bases

| Type of sequencing error | Sequencing error rate |
| --- | --- |
| A => C | 1.78E-06 |
| T => G | 1.13E-06 |
| A => G | 4.41E-06 |
| T => C | 6.96E-06 |
| A => T | 5.70E-06 |
| T => A | 2.97E-06 |
| C => A | 1.34E-05 |
| G => T | 2.91E-05 |
| C => G | 1.19E-05 |
| G => C | 1.92E-05 |
| C => T | 0.000153171 |
| G => A | 0.000443162 |

It could be seen from the above calculation results that the method had a single-base error rate ($10^{-5}$) far lower than the error rate of second-generation sequencing (1%), and far lower than those of the improved methods in the prior art as well. Thus, the method could thoroughly solve the error rate problem of the second-generation sequencing, and could implement ultra-accurate sequencing of DNA molecules by using second-generation sequencing techniques. Another merit of the present method is that the sequencing precision is irrelative to sequencing depth, which could solve problem that accurate sequencing of DNA sequence by labeling methods could be achieved only under very high sequencing coverage multipliers, so that accurate sequencing of large genome (such as human genome) could be achieved.

Example 6: Library Construction and Data Analysis for E. coli

DNAs of E. coli W3110 were collected, ultrasonically broken into DNA fragments with main band of 300 bp. 80~150 bp fragments were recovered, linked to tag sequences, converted into single strand, subjected to rolling circle amplification. After the rolling circle amplification, the DNAs were subjected to conventional second-generation sequencing library construction (see details in Example 1). About 4G of bi-directional data (read length was 2≤150=300 bp) were obtained by using hiseq 2500. The data were treated and analyzed as follows:

1. Measured in total: 13787730 reads, in which the number of reads capable of forming rings was: 7578585 reads.

2. Cyclization rate: 54.96615468971325%

3. For the formed rings, size range was: 30-260 bp, average size was: 122.909 bp, standard deviation was: 17.74147 bp. median was: 122 bp.

Sequencing error rates for bases were shown in Table 2.

TABLE 2

Sequencing error rates for different bases

| Type of sequencing error | Sequencing error rate |
| --- | --- |
| A => C | 2.66E-07 |
| T => G | 4.10E-07 |
| A => G | 2.79E-06 |
| T => C | 2.47E-06 |
| A => T | 1.58E-06 |
| T => A | 1.29E-06 |
| C => A | 5.68E-06 |
| G => T | 3.85E-06 |
| C => G | 3.20E-06 |
| G => C | 1.14E-06 |
| C => T | 0.000119 |
| G => A | 7.73E-05 |

Example 7: Construction and Data Analysis for Sequencing Library with Random Tag Sequences PhiX174 DNA was collected, ultrasonically broken into DNA fragments with main band at 100~200 bp. 60~100 bp fragments were recovered, linked to tag sequences, converted into single strand, subjected to rolling circle amplification. After rolling circle amplification, the DNA was subjected to conventional second-generation sequencing library construction (see details in Example 1). Wherein the tag sequences linked to the DNA fragments to be tested were as follows:

(SEQ ID NO: 14)
UO-adaptor 1N: 5'-pNNNNNNNNNNNTATGGGCAGTCGT-3'

(SEQ ID NO: 15)
UO-adaptor 2: 5'-CGACTGCCCATAG-3'.

About 4G of bi-directional data (read length was 2×150=300 bp) were obtained by using hiseq 2000. The data were treated and analyzed as follows:

1. Measured in total: 19147560 reads, in which the number of reads capable of forming rings (at least two repetitive units could be detected, similarly hereinafter) was: 4580270 reads.

2. Cyclization rate: 23.92090689361987%.

3. For the formed rings, size range (after removal of tag sequences) was: 1-133 bp, average size was: 88.56275 bp, standard deviation was: 29.17562 bp. median was: 98 bp.

Sequencing error rates for bases were shown in Table 3.

TABLE 3

Sequencing error rates for different bases

| Type of sequencing error | Sequencing error rate |
|---|---|
| A => C | 4.36E−07 |
| T => G | 9.22E−07 |
| A => G | 3.79E−06 |
| T => C | 4.12E−06 |
| A => T | 8.75E−06 |
| T => A | 1.24E−05 |
| C => A | 2.97E−05 |
| G => T | 1.93E−05 |
| C => G | 1.50E−05 |
| G => C | 9.99E−06 |
| C => T | 0.000103 |
| G => A | 0.000131 |

The method of the present invention is capable of performing ultra-accurate determination of DNA molecule composition in cells, and can relatively truly present DNA composition in normal or diseased (e.g., cancer tissues) cell colonies. In aspect of cancer detection, this method can be used for detection whether a tissue or organ of a normal individual has potential carcinogenic mutations so as to achieve the goal of finding cancers in advance and prophylaxis of cancers. In aspect of cancer studying, this method can be used to determine distribution of DNA mutations in cancer colonies; can be used to find potential small clone colonies in cancer tissues so as to realize heterogeneous structure of tumors; can help to illustrate effects of mutations in occurrence and development of cancers; and can be used to find tumor stem cells. In aspect of cancer therapy, this method can be used to find tumor stem cell colonies, and then a specific drug target can be designed for the tumor stem cells, so that effect therapy of cancer can be achieved. For normal individuals, this method can be used to detect DNA mutations in normal cells, so as to retrieve growth pattern of normal tissues; an can be used to determine numbers of DNA mutations in certain tissue of individuals with different ages, so as to estimate DNA mutation rates; or can be used to detect whether diseases-associated mutations exist in a normal individual, so as to achieve prophylaxis of diseases.

In the meantime, this method can be for effective library construction of free DNA in peripheral blood, and can effectively determine infrequent mutation sits in peripheral blood, and this kind of non-invasive detection method can be used for determination and evaluation of occurrence and development of cancers as well as harmful mutations in fetuses in antenatal diagnosis.

Ancient human DNA sequence is a main means for studying human evolution, but there are lots of problems in sequencing ancient human DNAs, among which the most serious problems are that the extracted ancient human DNAs have very low contents, are seriously degraded, and heavily contaminated. This method can construct libraries by using very small amounts of DNA (either single or double strands), and the constructed libraries can be used for exon trapping (removal of microorganism genome contaminations), and thus these problems in ancient DNA library construction can be effectively solved.

Although the specific embodiments of this invention have been described in details, those skilled in the art can understand that these details can be modified or changed according to the disclosed teachings, and all of these changes fall within the protection scope of the present invention. The protection scope of this invention is given by the appending claims and any equivalents thereof.

What is claimed is:

1. A method for preparing a sequencing library, comprising the following steps:
    (1) a sequence to be tested is linked to a tag sequence to obtain a double-strand or single-strand linked sequence;
    (2) when the linked sequence obtained in step (1) is a double-strand sequence, the linked sequence is converted into single-strand sequences, then cyclized; when the linked sequence obtained in step (1) is a single-strand sequence, the linked sequence is directly cyclized;

(3) the cyclized linked sequence obtained in step (2) is subjected to DNA amplification based on strand displacement reaction to obtain an equidirectional alternating concatemer consisting of the sequence to be tested and the tag sequence;

(4) the equidirectional alternating concatemer is fragmented, and sequencing adaptors are linked to both terminals of each resulted fragment to obtain a sequencing library;

wherein, the sum of the length of the sequence to be tested and the length of the tag sequence is less than half of the sequencing length of a sequencer; and the resulted fragment in step (4) has a length greater than the sequencing length of a sequencer;

the tag sequence is linked to the 5'-terminal of the sequence to be tested; and the equidirectional alternating concatemer comprises at least two repetitive units, and each repetitive unit comprises one sequence to be tested and one tag sequence.

2. The method according to claim 1, wherein the tag sequence comprises 4-20 consecutive determined bases and 0-18 consecutive random bases.

3. The method according to claim 2, wherein the determined bases and the random bases are arranged in a mode of sequential arrangement or mosaic arrangement.

4. The method according to claim 1, wherein the sequencing library is used for a second-generation sequencing or a third-generation sequencing.

5. A sequencing method, comprising a process of preparing a sequencing library, wherein the process for preparing the sequencing library comprises the following steps:

(1) a sequence to be tested is linked to a tag sequence to obtain a double-strand or single-strand linked sequence;

(2) when the linked sequence obtained in step (1) is a double-strand sequence, the linked sequence is converted into single-strand sequences, then cyclized; when the linked sequence obtained in step (1) is a single-strand sequence, the linked sequence is directly cyclized;

(3) the cyclized linked sequence obtained in step (2) is subjected to DNA amplification based on strand displacement reaction to obtain an equidirectional alternating concatemer consisting of the sequence to be tested and the tag sequence, that is, a sequencing library is prepared and obtained;

(4) the equidirectional alternating concatemer is fragmented, and sequencing adaptors are linked to both terminals of each resulted fragment to obtain a sequencing library;

wherein, the sum of the length of the sequence to be tested and the length of the tag sequence is less than half of the sequencing length of a sequencer; and the resulted fragment in step (4) has a length greater than the sequencing length of a sequencer;

the tag sequence is linked to the 5'-terminal of the sequence to be tested; and the equidirectional alternating concatemer comprises at least two repetitive units, and each repetitive unit comprises one sequence to be tested and one tag sequence.

6. The method according to claim 5, wherein the tag sequence comprises 4-20 consecutive determined bases and 0-18 consecutive random bases.

7. The method according to claim 6, wherein the determined bases and the random bases are arranged in a mode of sequential or mosaic arrangement.

8. The method according to claim 5, wherein the sequencing method is a second-generation sequencing method or a third-generation sequencing method.

9. The method according to claim 5, wherein the sequencing method is used for genomic DNA sequencing, target fragment trapping sequencing, single-strand DNA fragment sequencing, fossil DNA sequencing and sequencing of free DNA in body fluid.

10. The method according to claim 2, wherein the tag sequence comprises 6-13 consecutive determined bases.

11. The method according to claim 2, wherein the tag sequence comprises 0-13 consecutive random bases.

12. The method according to claim 3, wherein the determined bases are arranged in front of or behind the random bases.

13. The method according to claim 6, wherein the tag sequence comprises 6-13 consecutive determined bases.

14. The method according to claim 6, wherein the tag sequence comprises 0-13 consecutive random bases.

15. The method according to claim 7, wherein the determined bases are arranged in front of or behind the random bases.

16. The method according to claim 9, wherein said target fragment trapping sequencing is exon trapping sequencing.

17. The method according to claim 9, wherein said body fluid is blood, urine, or saliva.

* * * * *

SEQUENCE LISTING

<160> NUMBER OF SEQ ID NOS: 15

<210> SEQ ID NO 1
<211> LENGTH: 13
<212> TYPE: DNA
<213> ORGANISM: Artificial
<220> FEATURE:
<223> OTHER INFORMATION: UO-adaptor1

<400> SEQUENCE: 1
tatgggcagt cgt                                                         13

<210> SEQ ID NO 2
<211> LENGTH: 13
<212> TYPE: DNA
<213> ORGANISM: Artificial
<220> FEATURE:
<223> OTHER INFORMATION: UO-adaptor2

<400> SEQUENCE: 2
cgactgccca tag                                                         13

<210> SEQ ID NO 3
<211> LENGTH: 20
<212> TYPE: DNA
<213> ORGANISM: Artificial
<220> FEATURE:
<223> OTHER INFORMATION: Multiplexing Adaptor 1.0

<400> SEQUENCE: 3
gatcggaaga gcacacgtct                                           20

<210> SEQ ID NO 4
<211> LENGTH: 33
<212> TYPE: DNA
<213> ORGANISM: Artificial
<220> FEATURE:
<223> OTHER INFORMATION: Multiplexing Adaptor 2.0

<400> SEQUENCE: 4
acactctttc cctacacgac gctcttccga tct                            33

<210> SEQ ID NO 5
<211> LENGTH: 58
<212> TYPE: DNA
<213> ORGANISM: Artificial
<220> FEATURE:
<223> OTHER INFORMATION: MP PCR primer 1.0

<400> SEQUENCE: 5
aatgatacgg cgaccaccga gatctacact ctttccctac acgacgctct tccgatct   58

<210> SEQ ID NO 6
<211> LENGTH: 60
<212> TYPE: DNA
<213> ORGANISM: Artificial
<220> FEATURE:
<223> OTHER INFORMATION: MP index primer 1

<400> SEQUENCE: 6
caagcagaag acggcatacg agatcgtgat gtgactggag ttcagacgtg tgctcttccg   60

<210> SEQ ID NO 7
<211> LENGTH: 24
<212> TYPE: DNA
<213> ORGANISM: Artificial
<220> FEATURE:
<223> OTHER INFORMATION: MP PCR primer 2.0

<400> SEQUENCE: 7
caagcagaag acggcatacg agat                                      24

<210> SEQ ID NO 8
<211> LENGTH: 14
<212> TYPE: DNA
<213> ORGANISM: Artificial
<220> FEATURE:
<223> OTHER INFORMATION: primer UO-a3

<400> SEQUENCE: 8
acgactgccc atat                                                 14

<210> SEQ ID NO 9
<211> LENGTH: 19
<212> TYPE: DNA
<213> ORGANISM: Artificial
<220> FEATURE:
<223> OTHER INFORMATION: primer Epi_ME

<400> SEQUENCE: 9
ctgtctctta tacacatct                                            19

<210> SEQ ID NO 10
<211> LENGTH: 44
<212> TYPE: DNA

```
<213> ORGANISM: Artificial
<220> FEATURE:
<223> OTHER INFORMATION: Epi_Adaptor1

<400> SEQUENCE: 10
ctacacgcct ccctcgcgcc atcagagatg tgtataagag acag         44

<210> SEQ ID NO 11
<211> LENGTH: 44
<212> TYPE: DNA
<213> ORGANISM: Artificial
<220> FEATURE:
<223> OTHER INFORMATION: Epi_Adaptor2

<400> SEQUENCE: 11
cggtctgcct tgccagcccg ctcagagatg tgtataagag acag         44

<210> SEQ ID NO 12
<211> LENGTH: 48
<212> TYPE: DNA
<213> ORGANISM: Artificial
<220> FEATURE:
<223> OTHER INFORMATION: Epi_PCR primer 1.0

<400> SEQUENCE: 12
aatgatacgg cgaccaccga gatctacacg cctccctcgc gccatcag     48

<210> SEQ ID NO 13
<211> LENGTH: 55
<212> TYPE: DNA
<213> ORGANISM: Artificial
<220> FEATURE:
<223> OTHER INFORMATION: Epi_PCT index primer

<400> SEQUENCE: 13
caagcagaag acggcatacg agatcgtgat cggtctgcct tgccagcccg ctcag    55

<210> SEQ ID NO 14
<211> LENGTH: 22
<212> TYPE: DNA
<213> ORGANISM: Artificial
<220> FEATURE:
<223> OTHER INFORMATION: UO-adaptor1N
<220> FEATURE:
<221> NAME/KEY: misc_feature
<222> LOCATION: (1)..(9)
<223> OTHER INFORMATION: n is a, c, g, or t

<400> SEQUENCE: 14
nnnnnnnnnt atgggcagtc gt                                 22

<210> SEQ ID NO 15
<211> LENGTH: 13
<212> TYPE: DNA
<213> ORGANISM: Artificial
<220> FEATURE:
<223> OTHER INFORMATION: UO-adaptor2

<400> SEQUENCE: 15
cgactgccca tag                                           13
```